United States Patent [19]

Jonsson et al.

[11] Patent Number: 4,534,231

[45] Date of Patent: Aug. 13, 1985

[54] METHOD AND DEVICE FOR TAKING SOIL SAMPLES

[76] Inventors: Mats Jonsson; Per-Olof Edén, both of PL 1425, Bergeforsen, Sweden, 860 33

[21] Appl. No.: 506,372

[22] Filed: Jun. 21, 1983

[51] Int. Cl.³ .......................... G01N 1/06; E21B 49/02
[52] U.S. Cl. .................................. 73/864.43; 175/20; 175/58; 175/403; 175/404
[58] Field of Search ........... 73/864.45, 864.44, 864.43; 175/58, 403, 404, 244, 246, 247, 248, 249, 250, 253, 254, 296, 309, 236, 239, 240, 330, 332, 333, 20

[56] References Cited

U.S. PATENT DOCUMENTS

| | | |
|---|---|---|
| 257,896 | 5/1882 | Reichardt ........................ 175/333 X |
| 262,847 | 8/1882 | Stevens ............................. 73/864.43 |
| D. 269,844 | 7/1983 | Hackerson ....................... 175/249 X |
| 1,420,242 | 6/1922 | Christian ............................. 175/250 |
| 1,807,953 | 6/1931 | Anderson ............................ 175/250 |
| 1,927,871 | 9/1933 | Irwin et al. ....................... 73/864.43 |
| 2,634,956 | 4/1953 | Stokes ................................. 175/248 |
| 3,043,379 | 7/1962 | Porter et al. ..................... 175/253 X |
| 3,057,415 | 10/1962 | Cox ................................... 175/249 X |
| 3,123,163 | 3/1964 | Overby ............................... 175/404 |
| 3,375,891 | 4/1968 | Murati ................................. 175/403 |
| 4,345,484 | 8/1982 | Gould et al. ................... 73/804.44 X |
| 4,428,602 | 1/1984 | Lambot et al. ................. 175/236 X |

FOREIGN PATENT DOCUMENTS

| | | | |
|---|---|---|---|
| 2144045 | 3/1973 | Fed. Rep. of Germany ... 73/864.44 |
| 130446 | 12/1959 | U.S.S.R. ............................... 175/253 |
| 478217 | 7/1975 | U.S.S.R. ............................ 73/864.44 |
| 645050 | 1/1979 | U.S.S.R. ............................ 73/864.45 |
| 665235 | 5/1979 | U.S.S.R. ............................... 175/403 |
| 667853 | 6/1979 | U.S.S.R. ............................... 175/403 |

Primary Examiner—S. Clement Swisher
Assistant Examiner—Tom Noland
Attorney, Agent, or Firm—Cushman, Darby & Cushman

[57] ABSTRACT

A process and device for extracting soil samples, wherein a core sample is extracted from the ground which is to be analyzed and part of the soil is removed from the core for subsequent analysis or other aftertreatment. The core sample is removed from the ground and enclosed in an encasing (32, 34) in which the core sample remains in the form and position it had in the ground prior to extraction. The required volumes of soil samples are removed via openings (46) in the encasing (32, 34) at pre-determined points, and collected for further treatment.

12 Claims, 4 Drawing Figures

PERCUSSION DEVICE

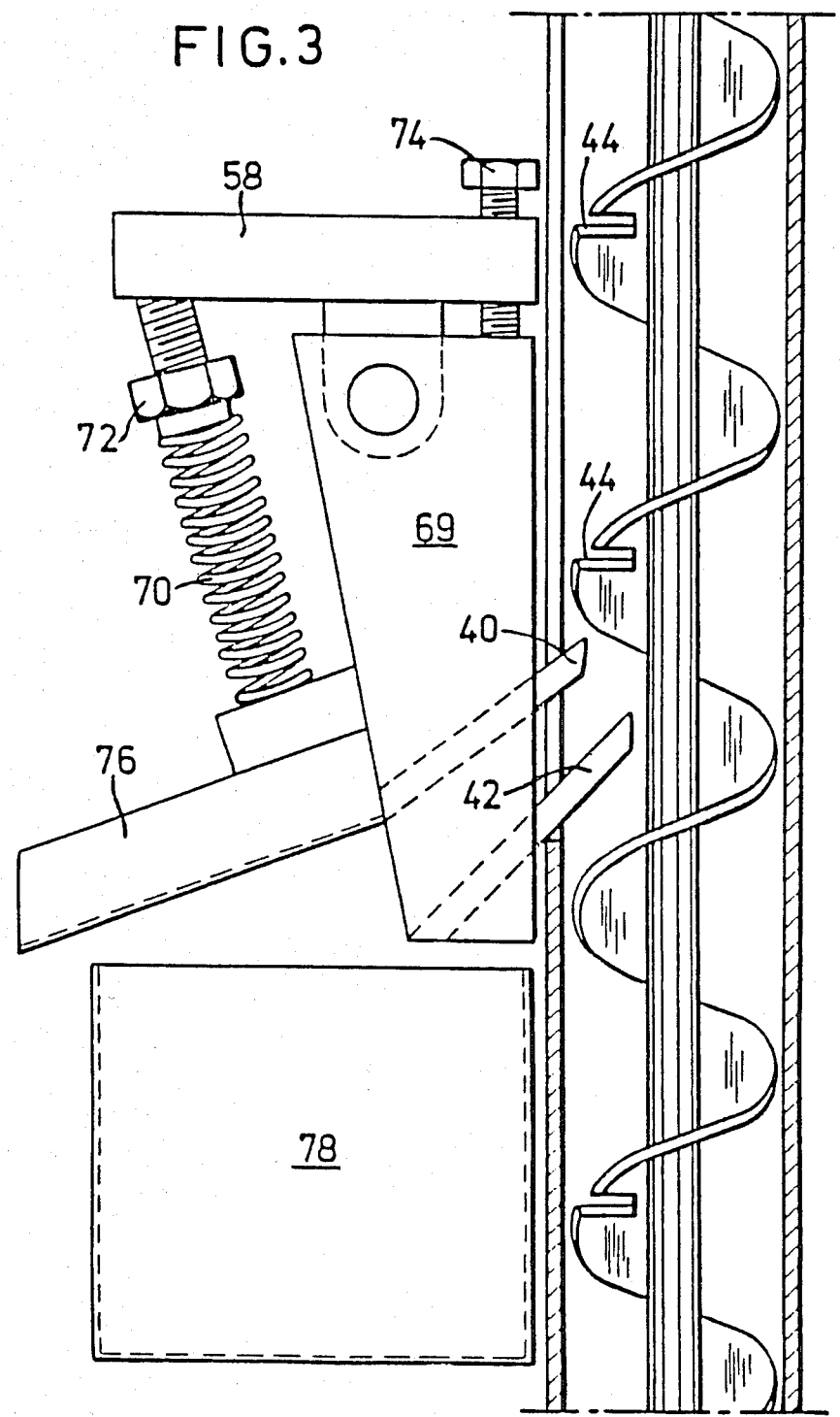

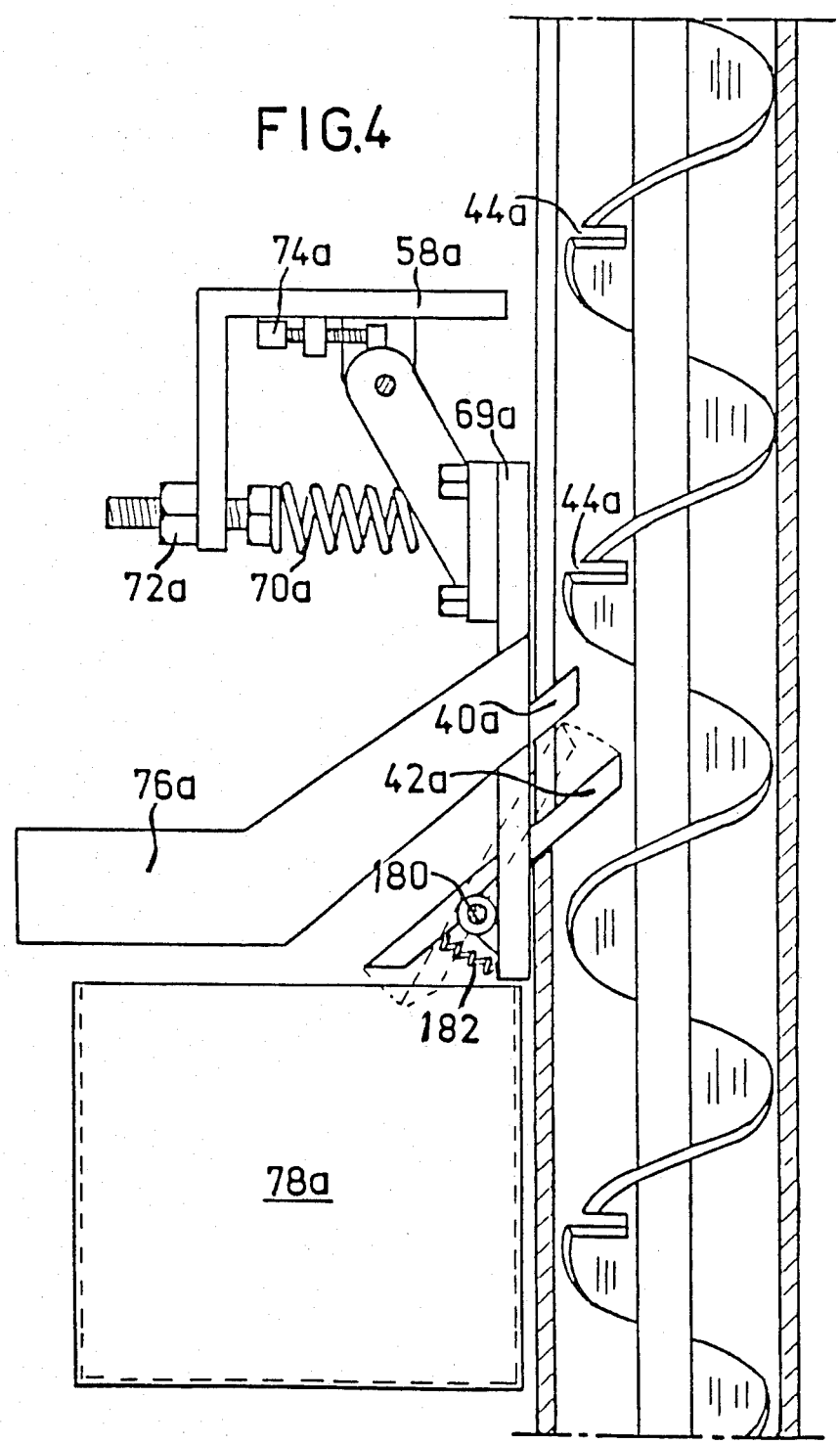

METHOD AND DEVICE FOR TAKING SOIL SAMPLES

BACKGROUND OF THE INVENTION

This invention relates to a process for taking soil samples, wherein a core sample is taken from the ground which is to be analysed, and a section of the soil is removed from the core for subsequent analysis or other after-treatment. The invention also relates to a device for the performance of this process.

In order to enable optimization of the yield of harvests within the agricultural industry, it is normal current practice to determine the soil's content of additives, such as fertilizers, by taking a number of soil samples from over a field and then to analyse them. Using the result of the analysis, it is possible to determine the type and quantity of additive to be put into the soil in order to improve the harvest yield. At the same time, the costs of fertilization and other soil treatments is reduced, as is also environmental damage, since no excess of additive is put into the soil. Sampling is normally carried out along at least one sampling line over the field, whereby, using a drill steel, screw conveyor or the like, core samples are extracted from a number of points, for example 20, along the sampling line, and, from the core samples extracted in this way, a required sample volume is removed from a number of points corresponding to various soil depths.

The results of sampling and the subsequent analysis are naturally dependent on the precision in the sampling process, i.e. the same volumes being taken at the same levels along the whole of the sampling line. To date, however, removing samples from the core has been carried out manually, which has not led to satisfactory reproducibility of the sampling process and has also resulted in a number of drawbacks in other respects. Manual removal of a required, suitable volume, for example about 50 cm$^3$, of sample has been performed by employing a tool to remove scrapings from the various levels of the core sample, which method, besides the disadvantage of the sampling process being time-consuming, has not provided precision in the sampling process. Thus the volume of sample scrapings has varied considerably, due to the difficulty of estimating the correct volume and because accompanying lumps of earth, stones, etc., have increased the volume to an indeterminable extent. Neither has it been possible to define exactly the levels on which the samples have been removed. In order to reduce handling time, removal of samples has had to be performed at the same time as moving the drilling equipment between the drilling points in the field, although this is further detrimental to accuracy, since the work has had to be performed at the same time as the equipment has been moving over the uneven surface of the field. A further disadvantage is that the residue of the core sample, after sample extraction, has had to be removed from the drill steel before the next drilling begins. This manual removal of the remains of the previous core sample is also time-consuming and laborious.

The main object of the invention is therefore to provide a process and device for taking of core samples, wherein these disadvantages are eliminated, so that it is possible for the rate of sampling to be substantially increased and precision improved, whereby the reliability of the test result obtained is improved considerably. These objects are achieved because the process and the device of the invention have been provided with the characteristics specified in the following patent claims.

BRIEF DESCRIPTION OF THE DRAWINGS

In the following, the invention will be described in greater detail, together with a preferred embodiment of a device for the performance of the method for taking samples.

FIG. 3 shows a longitudinal section through the drill steel enclosed by the encasing, together with one of the sampling mechanisms arranged on the encasing.

FIG. 4 shows a section through another embodiment.

DESCRIPTION OF THE PREFERRED EMBODIMENTS

Figure 1:
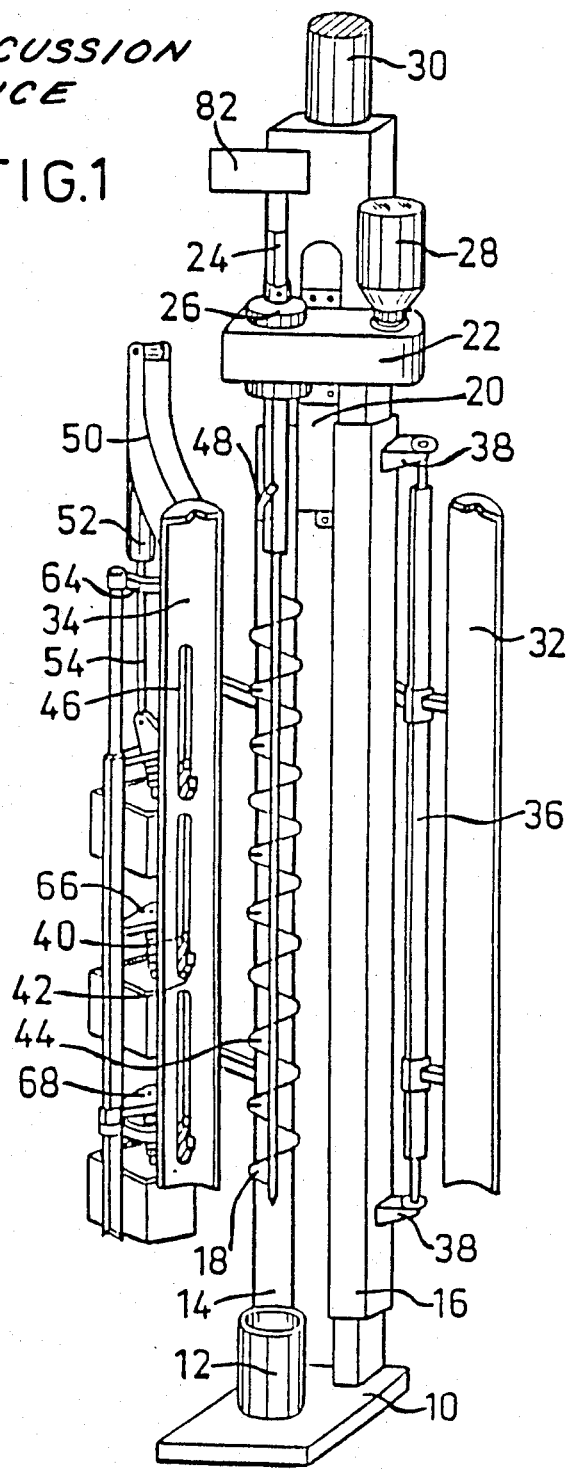
FIG. 1 is a perspective view of the essential part of the core sampling device, and the parts contained therein.

The core sampling device, illustrated in FIG. 1, comprises a base plate 10, which bears a tubular steering device 12, and two uprights 14 and 16. The steering device, 12, is arranged above a circular hole (not illustrated) in the base plate 10, and the inner diameter of the steering device and the hole corresponds to the outer diameter of the core sampling device's drill or screw 18, which is described in greater detail below. The uprights 14, 16 act as steering guides for a slide unit 20, which is movable in the longitudinal direction of the uprights 14, 16, and which in turn bears a drill holder 22. In the drill holder 22, the rear, squared end-fitting 24 of the drill 18, is pivoted in a bearing 26, which also incorporates a power connection, such as a cog wheel or chain transmission from a drive motor 28, for example a hydraulic motor also fitted on the drill holder 22. To the upper end 30 of the slide unit 20 is connected a control device (not illustrated), for example a hydraulic cylinder or motor, which during operation is disposed to move the slide unit 20 and therewith the drill holder 22 and the drill 18 fitted to it with drive motor 28, in the longitudinal direction of the uprights 14, 16 for raising and lowering of the drill. In FIG. 1, the slide unit 20 is shown in its uppermost position, and when the slide unit 20 is moved downwardly in the Figure, the drill 18 will pass through the steering device 12 and the hole in the base plate and down into the ground below, while at the same time the drill 18 is rotated via the drive motor in order to bore out a core sample.

It should be made clear that the drilling device shown is suitably arranged on a means of transport, such as a wagon or powered vehicle so as to be capable of being easily moved over the field in which the samples are to be taken. In this connection, the vehicle should be of the type with a low pressure of weight against the ground, which is normally achieved by the vehicle having several wheels, for example six, eight or more having a broad area of contact with the ground. Of course, tracked vehicles or the like may alternatively be used to carry the core sampling equipment illustrated in FIG. 1. The uprights 14, 16 and the drill 18 are of suitable lengths for the extraction of a core sample from the required depth, for example a depth of approximately 1 meter in the field.

After drilling, the drill 18 is raised with the soil (core sample) remaining in the turns, with the aid of the slide unit 20 and the hydraulic device connected thereto. When the drill 18 passes through steering device 12 on the plate 10, the soil outside the turns of the drill 18 will be scraped off, so that a core sample is obtained with the same outer diameter as the turn.

For the removal of the desired samples from the core sample extracted, an extraction mechanism is provided comprising two tube halves 32, 34 which are secured to axles 36, one of which is illustrated in FIG. 1. The axles 36 are in turn are swivel-mounted on brackets 38 secured to the uprights 14, 16 on the drilling device. The tube halves 32, 34 can be swivelled by means of a control mechanism, not illustrated in greater detail, from the open position shown in FIG. 1 to a position in which they enclose the drill 18 and the core sample extracted (see FIG. 3). The tube halves 32, 34 thus enclose, as shown in FIG. 3, in their swivelled-together position, the drill 18 and the core sample with extremely little play. In this way, the core sample extracted will be maintained in the dimensions and form which it had in the ground prior to extraction, and samples can be bored out without any soil falling off or changing position.

To remove soil samples from the enclosed core sample, a number of cutters 40, 42 are used, in the case illustrated three pairs of cutters which are movable vertically, i.e. in the longitudinal direction of the drill 18. In order for this movement along the core sample to be possible, the turns of the drill 18 are provided with a number of recesses 44, which are located opposite each other along the longitudinal direction of the drill. These recesses 44 have a width so much greater than the cutters 40, 42 that the cutters are able to pass unimpeded through the recesses 44. The cutters 40, 42 enter through slots 46 in the tube half 34 on which the extraction mechanism is fitted, and are moved along the slot 46 by a mechanism which is described in greater detail below.

In order to enable the soil samples to be removed in the way described, the recesses 44 in the drill 18 must be located opposite the slots 46 in tube half 34. This is achieved with the aid of a vane 48 fitted to the upper squared end-fitting 24 of the drill, which vane 48, when the drill 18 is stationary, is arranged to rest in the plane of the surface of division between the tube halves 32, 34, when the latter are swivelled into the position enclosing the drill 18. The prerequisite for this to function is that the vane 48, when rotation of the drill steel is stopped, comes to rest at some point within a total angle of about 120° around this plane, which prerequisite is achieved by the means of causing the drive motor 28 for the drill 18, when the drill is raised by the limit switch, to stop within the said angle range. When the tube halves 32, 34 are thereafter brought together, the vane will come into contact with the edge of one of the tube halves and will be brought into the position described above in the surface of division between the tube halves, by which means the position of the screw 18 is defined exactly in relation to the slots 46 and the cutters 40, 42. The position is also secured inasmuch as the squared end-fitting 24 is fixed into the corresponding recess in the tube halves. In order to enable the drill to be turned to the said position when the drive motor 28 has been stopped, the pressure fluid circuit for the drive motor 28 is suitably provided with a mechanical clutch or the like.

Figure 2:
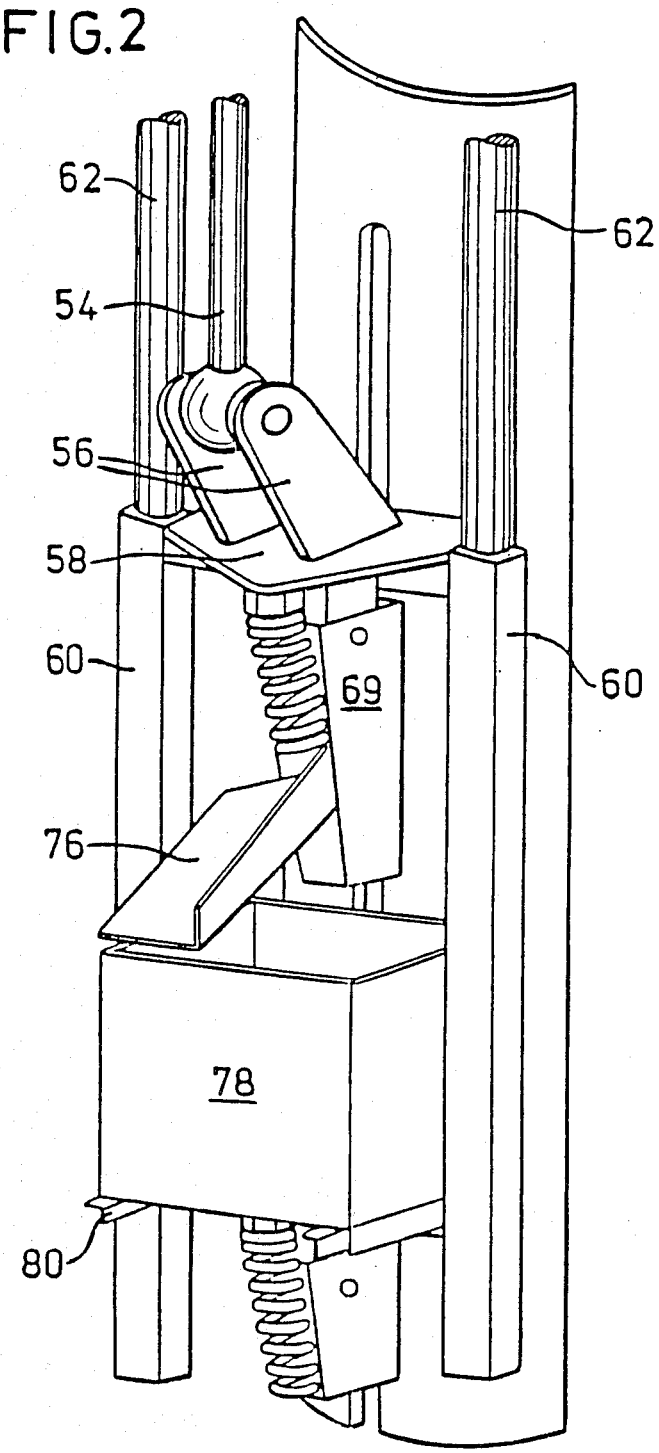
FIG. 2 is a perspective view of the rear of a section of an encasing shown in FIG. 1, which is used to enclose the core sample extracted, together with the sampling mechanism arranged on the reverse of the encasing.

The vertical movement of the cutters 40, 42, i.e. along the drill 18, is performed with the assistance of a hydraulic cylinder 52 with piston rod 54, which cylinder 52 is mounted in a bracket 50 arranged on tube half 34. The piston rod 54 is, as is shown in greater detail in FIG. 2, connected to a bearing bracket 56 arranged on a plate 58 which bears the uppermost sampling mechanism. The plate 58 is secured to a square tube 60 which slides along guides 62 which in turn are secured to tube half 34 by means of arms (FIG. 1). At an equal distance from the square tube 60, two further clamp plates 66, 68 are fitted for two further sampling mechanisms. Since all three sampling mechanisms on the plates 58, 66, 68 are identical, only one of them will be described in the following in relation to FIGS. 2 and 3.

Beneath the plate 58 is pivot-mounted a clamp 69, which at its lower end bears the cutters 40, 42 which enter through the slot 46 the tube half 34. The clamp 69 is held in the position shown in FIG. 3 by means of a spring 70 which is arranged between outer end of the plate 58 and the lower part of the clamp 69. The position of the clamp 69 in relation to the plate 58 can be adjusted using the adjustment screws 72, 74 shown in FIG. 3. The spring suspension allows the clamp 69 with the cutters 40, 42 to give way to the force from the spring 70 round the point of pivoting in the event that during upward movement of the mechanism along the slot 46, the cutters 40, 42 should come into contact with a stone or other hard object in the core sample.

The sampling mechanism described functions in the following way: when the tube halves 32, 34 have been closed around the drill 18 and the core sample found in the turns of the drill, the hydraulic cylinder 52 is actuated such that the square tube 60 and the sampling mechanisms fitted thereon move upwardly along the guides 62 along the drill 18. The upper cutter 40 thereby cuts away an approximately 7 mm deep layer of soil which is carried via the upper side of the cutter 40 and a channel 76 of sheet steel or a similar material arranged at the end 40 of the cutter, to a position outside the mechanism and falls away. This layer of soil, which is on the surface of the core sample and which contains impurities and surface soil (top soil), is not required in the sample, and thus is removed with the cutter 40 in the manner described. The lower cutter 42 cuts a further depth of 15 mm and a length of 250 mm, removing thereby a soil sample, which is carried along the upper side of the cutter 42 to, and falls down into a removable tray or box 78 which is disposed below the end of the cutter 42, for example on a holder 80. The 3 sampling mechanisms shown are suitably arranged such that the cutters remove samples from the core sample within areas on different depths in the soil.

After removal of the soil samples, the tube halves 32, 34 are swivelled apart to the position illustrated in FIG. 1 and the hydraulic cylinder 52 returns the sampling mechanisms to the lower position also illustrated in FIG. 1. While the wagon or truck carrying the drilling equipment is being moved to the next sampling location, the residues of the core sample are removed, which is suitably performed by means of an in itself known percussion device 82, which is illustrated diagrammatically above the upper end 24 of the drill 18, and whose impact is applied axially on the drill, by which means any residual core sample is effectively removed from the turn. The device may be replaced by other suitable mechanisms.

In the embodiment shown in FIG. 4 the parts corresponding to the embodiment in FIG. 3 have the addition of an "a". The difference between FIGS. 3 and 4 lies in the fact that the lower cutter 42a is swingably journalled on the pin 180. A spring 182 biases the cutter 42a into the position shown with unbroken lines in FIG. 4. When the square tube 60 and the sampling mechanism fitted thereon are in the lowest position and the tube halves 32,34 are closed around the drill 18, the cutter 42a will be swung towards the position engaging the cutter 40a, as shown with dotted lines in FIG. 4, due to contacting the lower edge of the slot in the tube half. Soil cannot then enter the space between the cutters 40a and 42a so that contaminated soil will not fall into the box 78a. When the sampling mechanisms are moved upwardly the cutter 42a is forced into the position shown by unbroken lines in FIG. 4 by spring 182 and will cut uncontaminated soil from a position deeper in the soil column. Soil from the surface which possibly may contain impurities will thus not be cut out.

From the above, it is evident that a sampling device has been obtained which offers a number of advantages. The enclosing of the core sample during extraction provides the maximum guarantee that the sample will reproduce exactly the conditions at the corresponding location in the ground. As the samples are taken in a vertical direction, a representative sample is obtained for the whole level despite the smallness of the sample volume, while sampling at several strictly defined levels allows the possibility of separate analysis of the samples. The sample volume extracted on each occasion, approximately 20 cm$^3$, which is determined by the dimensions of the cutter 42 is very precise, since no lumps of earth or the like can affect the sampling process, which is thus uninfluenced by the nature of the ground.

Even if the device has been described as being powered by pressure fluid, such as hydraulic fluid, it is clear that other sources of power are conceivable, also including, for example, manual operation of the mechanisms. It is thus clear that the illustrated and described embodiment is only an example of application of the invention and that this can be modified and varied within the scope of the following patent claims.

We claim:

1. A process of taking soil samples which are to be analyzed wherein a core sample is extracted from the ground and the soil sample removed from the core sample, the process comprising taking a core sample using an auger-type drill by drilling to a predetermined depth, stopping rotation of the drill, removing the drill and core sample from the ground, enclosing the core sample with a casing to maintain the core sample in the same form and position as found in the ground, the casing including openings corresponding to different layers in the core sample, removing a soil sample through the openings in the casing.

2. A process as described in claim 1, wherein the removal of the soil sample is carried out in a vertical direction.

3. A process as described in claim 1 wherein the soil samples are removed simultaneously at several levels in the core sample.

4. An apparatus for taking soil samples from a core sample comprising an auger drill where each turn of the drill threads is provided with a recess, each recess lying in the same longitudinal plane of the drill, the drill capable of drilling and removing a core sample from the ground, a casing means for surrounding the core sample thereby maintaining the core sample in the same form as in the ground, the casing having at least one longitudinal slot, at least one cutter to be inserted through the slot to remove a soil sample, the cutter being supported on a hoisting means for vertical movement within the slot and through the recesses of the drill, at least one container arranged to receive the soil sample as it is removed by the cutter.

5. An apparatus according to claim 4, wherein the casing comprises two tube halves, which can be swivelled between an open position where the tube halves have been drawn apart and a closed position in which the drill is enclosed.

6. An apparatus according to claim 4, being characterized in that the drill can be raised and lowered on a frame provided with a steering means for the drill, which steering means also serves as a scraper for material found outside the thread of the drill.

7. An apparatus according to claim 4, wherein the drill has a stopping means which stops the drill in a precisely defined location, where the recesses are positioned right in front of the slots in the encasing.

8. An apparatus according to claim 7, wherein the stopping device includes a vane fitted on the axle of the drill, which vane is set up to be brought by either of the tube halves into a position where the recesses in the drill lie right in front of the slots in the casing.

9. An apparatus according to claim 4, wherein the cutter is spring biased toward the slot and capable of moving outwardly from the slot when the cutter contacts a hard object.

10. An apparatus for taking soil samples from a core sample comprising a drill wherein each turn of the drill threads is provided with a recess, each recess lying in the same plane, the plane being parallel to the longitudinal axis of the drill, the drill being capable of drilling and removing a core sample from the ground, a casing for surrounding the core sample thereby maintaining the core sample in the same form as in the ground, the casing having at least one slot in the longitudinal direction, at least one cutter to be inserted through the slot to remove a soil sample, the cutter comprising a first cutting means to remove and discard a first layer of soil from the core sample, a second cutter means trailing the first cutter and being longer than the first cutter to remove a soil sample from the core sample and direct the soil sample to a container, the cutter being supported on a hoisting means for vertical movement within the slot and through the recesses of the drill.

11. An apparatus according to claim 10, wherein the second cutter for removing the soil sample is swingably journalled and biased towards the soil removing position.

12. An apparatus according to claim 10 wherein the second cutter is swingably journalled and biased towards the soil removing position.

* * * * *